United States Patent
Miyamoto et al.

(10) Patent No.: US 10,005,766 B2
(45) Date of Patent: Jun. 26, 2018

(54) METHOD FOR PRODUCING FUSED HETEROCYCLIC COMPOUND

(71) Applicant: Sumitomo Chemical Company, Limited, Chuo-Ku, Tokyo (JP)

(72) Inventors: Takashi Miyamoto, Osaka (JP); Daisuke Sasayama, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days. days.

(21) Appl. No.: 15/320,907

(22) PCT Filed: May 28, 2015

(86) PCT No.: PCT/JP2015/066126
§ 371 (c)(1),
(2) Date: Dec. 21, 2016

(87) PCT Pub. No.: WO2015/198817
PCT Pub. Date: Dec. 30, 2015

(65) Prior Publication Data
US 2017/0158682 A1    Jun. 8, 2017

(30) Foreign Application Priority Data
Jun. 26, 2014 (JP) .................. 2014-131037

(51) Int. Cl.
*C07D 413/04* (2006.01)
*C07D 213/62* (2006.01)
(Continued)

(52) U.S. Cl.
CPC ......... *C07D 413/04* (2013.01); *C07D 213/62* (2013.01); *C07D 213/78* (2013.01); *C07D 213/81* (2013.01)

(58) Field of Classification Search
CPC .. C07D 413/04; C07D 213/62; C07D 213/78; C07D 213/81
See application file for complete search history.

(56) References Cited

FOREIGN PATENT DOCUMENTS

| | | |
|---|---|---|
| CN | 103717598 A | 4/2014 |
| DE | 262883 C | 7/1913 |

(Continued)

OTHER PUBLICATIONS

Int'l Search Report dated Aug. 21, 2015 in Int'l Application No. PCT/JP2015/066126.
(Continued)

*Primary Examiner* — D Margaret M Seaman

(74) *Attorney, Agent, or Firm* — Panitch Schwarze Belisario & Nadel LLP

(57) ABSTRACT

A compound represented by formula (4) is produced by a step A of reacting a compound represented by formula (2):

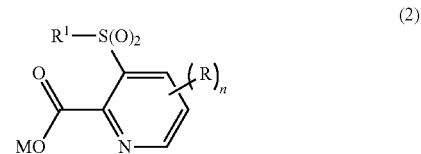

wherein $R^1$ represents an ethyl group or the like, R represents a halogen atom or the like, n represents 0, 1, 2, or 3, and M represents potassium or the like, with thionyl chloride to obtain a compound represented by formula (1):

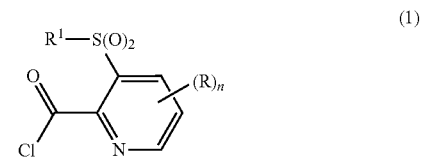

a step B of reacting the compound represented by formula (1) with a compound represented by formula (5):

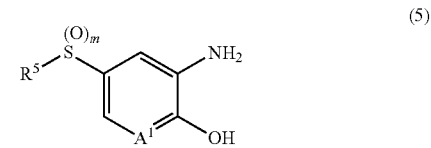

wherein $A^1$ represents a nitrogen atom or =CH—, $R^5$ represents a trifluoromethyl group or the like, and m represents 1 or 2, to produce a compound represented by formula (3):

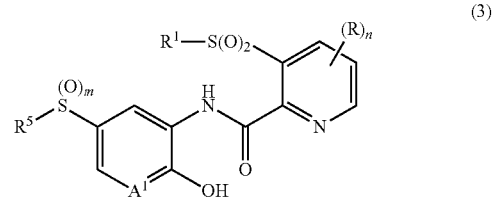

or an acid salt thereof; and a step C of reacting the compound represented by formula (3) or an acid salt thereof in the presence of acid at 100° C. to 180° C. to obtain the compound represented by formula (4):

(Continued)

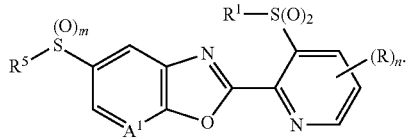

(4)

7 Claims, No Drawings

(51) Int. Cl.
C07D 213/78 (2006.01)
C07D 213/81 (2006.01)

(56) References Cited

FOREIGN PATENT DOCUMENTS

WO 2013/018928 * 2/2013
WO 2013018928 A1 2/2013

OTHER PUBLICATIONS

Int'l Preliminary Report on Patentability dated Dec. 27, 2016 in Int'l Application No. PCT/JP2015/066126.
Schnettler et al, "4-Aroyl-1,3-Dihydro-2H-Imidazol-2-Ones: A New Class of Cardiotonic Agents. 2. Effect of 4-Pyridoyl Substituents and Related Compunds," Journal of Medicinal Chemistry, vol. 29, No. 5, pp. 860-862 (1986).
Office Action dated Mar. 27, 2018 in CN Application No. 201580033836.4.

* cited by examiner

METHOD FOR PRODUCING FUSED HETEROCYCLIC COMPOUND

CROSS-REFERENCE TO RELATED APPLICATION

This application is a Section 371 of International Application No. PCT/JP2015/066126, filed May 28, 2015, which was published in the English language on Dec. 30, 2015, under International Publication No. WO 2015/198817 A1, and the disclosure of which is incorporated herein by reference.

TECHNICAL FIELD

The present invention relates to a method for producing a fused heterocyclic compound.

BACKGROUND ART

It is mentioned that fused heterocyclic compounds including 2-(3-ethylsulfanylpyridin-2-yl)-5-trifluoromethylbenzoxazole have excellent control efficacy again at pests, and Production process 2 mentions a synthesis method in which an amide compound is synthesized by reacting an aminophenol compound with a pyridinecarboxylic chloride compound and then the amide compound is subjected to ring closure in WO 2013/018928.

It is also mentioned that potassium isonicotinate reacts with oxalyl chloride to produce isonicotinoyl chloride in Journal of Medicinal Chemistry, 29, 860-862 (1986).

DISCLOSURE OF THE INVENTION

The present invention provides a method for producing a compound represented by formula (4):

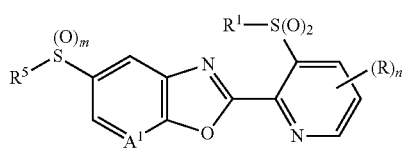

(4)

wherein
$R^1$ represents a chain hydrocarbon group having 1 to 6 carbon atoms which is optionally halogenated, or an alicyclic hydrocarbon group having 3 to 6 carbon atoms which is optionally halogenated,
R each independently represents a chain hydrocarbon group having 1 to 6 carbon atoms which is optionally halogenated, or a halogen atom,
$R^5$ represents a chain hydrocarbon group having 1 to 6 carbon atoms which is optionally halogenated, or an alicyclic hydrocarbon group having 3 to 6 carbon atoms which is optionally halogenated,
$A^1$ represents a nitrogen atom or =CH—,
m represents 1 or 2, and
n represents 0, 1, 2, or 3,
The present invention is typically as follows.
[1] A method for producing a compound represented by formula (4), which comprises a step A of reacting a compound represented by formula (2):

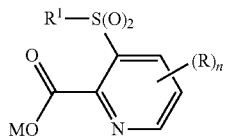

(2)

wherein
$R^1$ represents a chain hydrocarbon group having 1 to 6 carbon atoms which is optionally halogenated, or an alicyclic hydrocarbon group having 3 to 6 carbon atoms which is optionally halogenated,
R each independently represents a chain hydrocarbon group having 1 to 6 carbon atoms which is optionally halogenated, or a halogen atom, n represents 0, 1, 2, or 3, and M represents sodium, potassium, or lithium, with thionyl chloride to obtain a compound represented by formula (1):

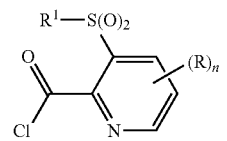

(1)

wherein $R^1$, R, and n have the same meanings as defined above (hereinafter referred to as the step A);
a step B of reacting the compound represented by formula (1) with a compound represented by formula (5):

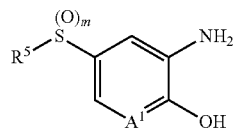

(5)

wherein
$A^1$ represents a nitrogen atom or =CR—,
$R^5$ represents a chain hydrocarbon group having 1 to 6 carbon atoms which is optionally halogenated, or an alicyclic hydrocarbon group having 3 to 6 carbon atoms which is optionally halogenated, and m represents 1 or 2, to produce a compound represented by formula (3):

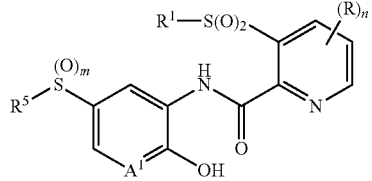

(3)

wherein $R^1$, R, $R^5$, $A^1$, m, and n have the same meanings as defined above (hereinafter referred to as the step B); and
a step C of reacting the compound represented by formula (3) or an acid salt thereof in the presence of an acid 100° C. to 180° C. to obtain the compound represented by formula (4):

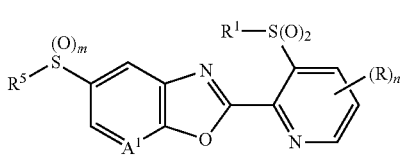

(4)

wherein $R^1$, R, $R^5$, $A^1$, m, and n have the same meanings as defined above (hereinafter referred to as the step C).

[2] The production method according to [1], wherein the acid in the step C is a sulfonic acid compound.

[3] The production method according to [1], wherein the acid in the step C is p-toluenesulfonic acid.

[4] The production method according to [1], wherein the acid in the step C is methanesulfonic acid.

[5] A method for producing a compound represented by formula (3) or an acid salt thereof, which comprises the step A of reacting a compound represented by formula (2):

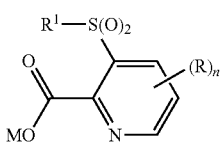

(2)

wherein
$R^1$ represents a chain hydrocarbon group having 1 to 6 carbon atoms which is optionally halogenated, or an alicyclic hydrocarbon group having 3 to 6 carbon atoms which is optionally halogenated,
R each independently represents a chain hydrocarbon group having 1 to 6 carbon atoms which is optionally halogenated, or a halogen atom, n represents 0, 1, 2, or 3, and M represents sodium, potassium, or lithium, with thionyl chloride to obtain a compound represented by formula (1):

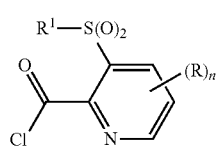

(1)

wherein $R^1$, R, and n have the same meanings as defined above; and the step B of reacting the compound represented by formula (1) with a compound represented by formula (5):

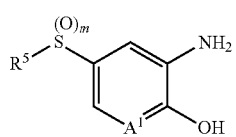

(5)

wherein
$A^1$ represents a nitrogen atom or =CH—,
$R^5$ represents a chain hydrocarbon group having 1 to 6 carbon atoms which is optionally halogenated, or an alicyclic hydrocarbon group having 3 to 6 carbon atoms which is optionally halogenated, and m represents 1 or 2, to produce the compound represented by formula (3):

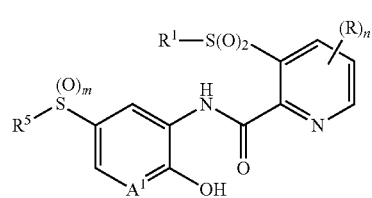

(3)

wherein $R^1$, R, $R^5$, $A^1$, m, and n have the same meanings as defined above.

[6] The production method according to any one of [1] to [5], wherein the solvent used in the step B contains an ether solvent.

[7] A method for producing a compound represented by formula (1), which comprises the step A of reacting a compound represented by formula (2):

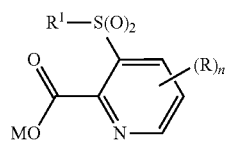

(2)

wherein
$R^1$ represents a chain hydrocarbon group having 1 to 6 carbon atoms which is optionally halogenated, or an alicyclic hydrocarbon group having 3 to 6 carbon atoms which is optionally halogenated,
R each independently represents a chain hydrocarbon group having 1 to 6 carbon atoms which is optionally halogenated, or a halogen atom, n represents 0, 1, 2, or 3, and M represents sodium, potassium, or lithium, with thionyl chloride to obtain the compound represented by formula (1):

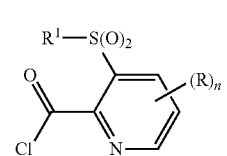

(1)

wherein $R^1$, R, and n have the same meanings as defined above.

Embodiments of the Invention

A compound represented by formula (1), a compound represented by formula (3), and a compound represented by formula (4) can be produced, for example, by the following production methods.

In the present invention, the halogen atom represents a fluorine atom, a chlorine, atom, a bromine, atom, and an iodine atom.

In the present invention, the chain hydrocarbon group having 1 to 6 carbon atoms represents an alkyl group having 1 to 6 carbon atoms, such as a methyl group, an ethyl group, a propyl group, an isopropyl group, and a hexyl group; an alkenyl group having 1 to 6 carbon atoms, such as a vinyl group, a 1-propenyl group, a 2-propenyl group, and a 1-hexenyl group; and an alkynyl group having 1 to 6 carbon atoms, such as an ethynyl group, a propargyl group, a 1-pentynyl group, and a 1-hexynyl group.

In the present invention, examples of the chain hydrocarbon group having 1 to 6 carbon atoms which is optionally halogenated include a C1-C6 alkyl group optionally having a halogen atom(s), such as a methyl group, an ethyl group, an isopropyl group, a butyl group, a tert-butyl group, a hexyl group, a fluoromethyl group, a chloromethyl group, a bromomethyl group, an iodomethyl group, a difluoromethyl group, a dichloromethyl group, a trifluoromethyl group, a trichloromethyl group, a 2-fluoroethyl group, a 2-chloroethyl group, a 2,2-difluoroethyl group, a 2,2,2-trifluoroethyl group, a pentafluoroethyl group, and a heptafluoropropyl group;
a C2-C6 alkenyl group optionally having a halogen atom(s), such as a vinyl group, a 2-propenyl group, a 1-methylvinyl group, a 2-methyl-1-propenyl group, a 3-butenyl group, a 1-hexenyl group, a 1,1-difluoroallyl group, and a pentafluoroallyl group; and a C2-C6 alkynyl group optionally having a halogen atom(s), such as an ethynyl group, a propargyl group, a 3-butynyl group, a 1-hexynyl group, and a 4,4,4-trifluoro-2-butynyl group.

In the present invention, the alicyclic hydrocarbon group having 3 to 6 carbon atoms represents a cycloalkyl group having 3 to 6 carbon atoms, such as a cyclopropyl group, a cyclobutyl group, and a cyclohexyl group; and a cycloalkenyl group having 3 to 6 carbon atom, such as a 1-cyclohexenyl group and a 3-cyclohexenyl group.

In the present invention, examples of the sulfonic acid compound include p-toluenesulfonic acid, benzenesulfonic acid, methanesulfonic acid, and camphorsulfonic acid.

In the present invention, examples of the amide solvent include N,N-dimethylformamide, N,N-dimethylacetamide, and N-methylpyrrolidone.

In the present invention, examples of the ether solvent include tetrahydrofuran, ethylene glycol dimethyl ether, tert-butyl methyl ether, and 1,4-dioxane.
(Step A)
A compound represented by formula (1) (hereinafter referred to as the compound (1)) can be produced by reacting a compound represented by formula (2) (hereinafter referred to as the compound (2)) with thionyl chloride.

The reaction is usually carried out in a solvent. Examples of the solvent used in the reaction include an aromatic hydrocarbon solvent such as toluene, xylene, ethylbenzene, and chlorobenzene; a halogen-containing aliphatic hydrocarbon solvent such as chloroform and dichloromethane; an ether solvent such as tetrahydrofuran, ethylene glycol dimethyl ether, tert-butyl methyl ether, and 1,4-dioxane; an ester solvent such as ethyl acetate and butyl acetate; a nitrile solvent such as acetonitrile and propionitrile; an aromatic heterocyclic solvent such as pyridine; a sulfur-containing compound solvent such as dimethyl sulfoxide and sulfolane; an amide solvent such as N,N-dimethylformamide, N,N-dimethylacetamide, and N-methylpyrrolidone; and mixed solvents thereof. The solvent is preferably an aromatic hydrocarbon solvent, a halogen-containing aliphatic hydrocarbon solvent, an ester solvent, an amide solvent, and mixtures thereof, more preferably an aromatic hydrocarbon solvent, an amide solvent, and mixtures thereof, and most preferably N,N-dimethylformamide.

The amount of the solvent to be used is usually 0 to 100 parts by mass, and preferably 1 to 20 parts by mass, based on 1 part by mass of the compound (2).

In the reaction, thionyl chloride is usually used in the proportion of 1 to 15 mol, and preferably 1 to 5 mol, based on 1 mol of the compound (2).

The reaction temperature of the reaction is usually within a range of 0 to 150° C., and preferably 0 to 80° C.

The reaction time of the reaction is usually within a range of 0.1 to 24 hours, and preferably 0.1 to 12 hours.

After completion of the reaction, the resulting compound may be used as it is for the step B after removing excess thionyl chloride by distillation, or may be purified by distillation. The compound (1) can be isolated by removing by-produced lithium chloride, sodium chloride, or potassium chloride by filtration, and concentrating the filtrate.

The compound (2) can be produced by reacting a 2-pyridinecarboxylic acid of formula:

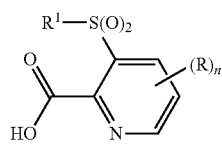

with an inorganic base such as alkali metal hydroxide (sodium hydroxide, potassium hydroxide and lithium hydroxide), alkali metal carbonate (sodium carbonate, potassium carbonate and lithium carbonate) and alkali metal hydrogen carbonate (sodium hydrogen carbonate, potassium hydrogen carbonate and lithium hydrogen carbonate) in a solvent such as an alcohol solvent (methanol, ethanol, 2-propanol and so on).
(Step B)
A compound represented by formula (3) (hereinafter referred to as the compound (3)) can be produced by reacting the compound (1) with a compound represented by formula (5) (hereinafter referred to as the compound (5)).

The reaction is usually carried out in a solvent. Examples of the solvent used in the reaction include an aromatic hydrocarbon solvent such as toluene, xylene, ethylbenzene, and chlorobenzene; a halogen-containing aliphatic hydrocarbon solvent such as chloroform and dichloromethane; an ether solvent such as tetrahydrofuran, ethylene glycol dimethyl ether, tert-butyl methyl ether, and 1,4-dioxane; an ester solvent such as ethyl acetate and butyl acetate; a nitrile solvent such as acetonitrile and propionitrile; an aromatic heterocyclic solvent such as pyridine; a sulfur-containing compound solvent such as dimethyl sulfoxide and sulfolane; an amide solvent such as N,N-dimethylformamide, N,N-dimethylacetamide, and N-methylpyrrolidone, and mixed solvents thereof. The solvent is preferably a solvent containing an ether solvent, and more preferably a solvent containing tetrahydrofuran.

The amount of the solvent to be used is usually 1 to 100 parts by mass, and preferably 1 to 20 parts by mass, based on 1 part by mass of the compound (1).

In the reaction, a base is optionally added. Examples of the base used in reaction include alkali metal carbonates such as sodium carbonate and potassium carbonate; alkali metal hydrogen carbonates such as sodium hydrogen carbonate and potassium hydrogen carbonate; and tertiary amines such as triethylamine, N,N-diisopropylethylamine, 1,4-diazabicyclo[2.2.2]octane, 1,8-diazabicyclo[5.4.0]undecene, pyridine, and 4-dimethylaminopyridine.

In the reaction, the compound (1) is usually used in the proportion of 1 to 3 mol and the base is usually used in the proportion of 1 to 10 mol, based on 1 ml of the compound (5). Preferably, the compound (1) is usually used in the proportion of 1 to 1.5 mol and the base is usually used in the proportion of 1 to 3 mol.

The reaction temperature of the reaction is usually within a range of −20 to 100° C. and preferably 0 to 80° C. The reaction time of the reaction is usually within a range of 0.1 to 24 hours, and preferably 0.1 to 12 hours.

After completion of the reaction, a hydrochloride is formed in the compound (3) and the hydrochloride of the compound (3) may be isolated by removing the precipitated crystal through filtration, and then the compound may be used as it is for the step C. When using for the step C without isolation, the compound may be used for the step C after substitution with a solvent having a boiling point of 100° C. or higher.

The compound (3) can be isolated by subjecting to post treatment operations such as addition of water to the reaction mixture, optional neutralization of the mixture with a base such as an aqueous sodium hydrogen carbonate solution, and extraction of the mixture with an organic solvent, followed by drying and concentration of the organic layer. It is also possible to further purify the isolation compound (3) by chromatography, recrystallization and the like. The compound (3) can be taken out in the form of a hydrate, and can be used as it is for the step C.

The compound (3) can be taken out in the form of a salt by mixing with an inorganic acid such as sulfuric acid, hydrochloric acid, hydrobromic acid, and hydroiodic acid, and a sulfonic acid compound such as p-toluenesulfonic acid, benzenesulfonic acid, methanesulfonic acid, and camphorsulfonic acid, and can be used as it is for the step C.

(Step C)

A compound represented by formula (4) (hereinafter referred to as the compound (4)) can be produced by reacting the compound (3) or an acid salt thereof in the presence of an acid at 100° C. to 180° C.

Examples of the acid used in the reaction include an inorganic acid such as sulfuric acid, hydrochloric acid, hydrobromic acid, and hydroiodic acid; a sulfonic acid compound such as p-toluenesulfonic acid, benzenesulfonic acid, methanesulfonic acid, and camphorsulfonic acid; or an Amberlite (registered trademark) acidic ion exchange resin. The acid is preferably a sulfonic acid compound, and more preferably paratoluenesulfonic acid and methanesulfonic acid.

The reaction is usually carried out in a solvent. Examples of the solvent used in the reaction include an aromatic hydrocarbon solvent such as toluene, xylene, ethylbenzene, chlorobenzene, cumen, mesitylene, and dichlorobenzene; an ether solvent such as 1,4-dioxane; an ester solvent such as butyl acetate; a nitrile solvent such as propionitrile; an aromatic heterocyclic solvent such as pyridine; a sulfur-containing compound solvent such as dimethyl sulfoxide and sulfolane; an amide solvent such as N,N-dimethylformamide, N,N-dimethylacetamide, and N-methylpyrrolidone; and mixed solvents thereof. The solvent is preferably an aromatic hydrocarbon solvent, and more preferably xylene and chlorobenzene.

The amount of the solvent to be used is usually 1 to 100 parts by mass, and preferably 1 to 20 parts by mass, based on 1 part by mass of the compound (3).

In the reaction, the acid is usually used in the proportion of 0.1 mol to 5 mol, and preferably 0.5 mol to 3 mol, based on 1 mol of the compound (3).

The reaction temperature of the reaction is usually within a range of 100 to 180° C., and preferably 100 to 160° C. The reaction time of the reaction is usually within a range of 0.1 to 48 hours, and preferably 0.1 to 24 hours.

In the reaction, water contained in raw materials and water produced during the reaction are preferably removed. Examples of the removing method includes a method in which water is removed by azeotropic dehydration using a Dean-Stark apparatus or the like, and a method in which water is removed by using a dehydrating agent such as molecular sieves, anhydrous sodium sulfate, and anhydrous magnesium sulfate, and the removing method is preferably a method in which water is removed by azeotropic dehydration.

In the reaction, an adsorbent such as activated carbon, silica gel, and Celite (registered trademark) may be added for the purpose of removing a decomposition product.

After completion of the reaction, the compound (4) can be isolated by adding the reaction mixture to water or an aqueous base such as aqueous alkali carbonate (e.g., $Na_2CO_3$, $K_2CO_3$) and aqueous alkali hydrogen carbonate (e.g., $NaHCO_3$, $KHCO_3$), extracting the mixture with an organic solvent, and concentrating the organic layer; collecting a solid, which is produced by adding the reaction mixture to water, by filtration; or collecting a solid produced in the reaction mixture by filtration. It is also possible to further purify the isolation compound (4) by chromatography, recrystallization and the like. The compound (4) can be taken out in the form of a salt by mixing with an inorganic acid such as hydrochloric acid, hydrobromic acid, and hydroiodic acid, and a sulfonic acid compound such as p-toluenesulfonic acid, benzenesulfonic acid, methanesulfonic acid, and camphorsulfonic acid.

EXAMPLES

The present invention will be further described by way of Examples, but the present invention is not limited to these Examples.

Example 1

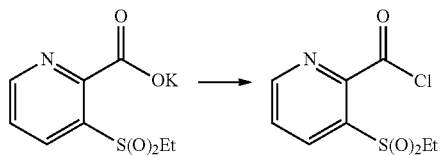

Under a nitrogen atmosphere, 0.50 g of potassium (3-ethylsulfonyl)-2-pyridinecarboxylate, 2.50 g of xylene, and 0.01 g of N,N-dimethylformamide were mixed and heated to 60° C., and then 0.35 g of thionyl chloride was added dropwise over 5 hours, followed by stirring at 60° C. for 4 hours. To the reaction solution, isobutylamine was added and quantitative determination was carried out by an internal reference method (internal reference substance; biphenyl) using high-performance liquid chromatography to obtain (3-ethylsulfonyl)-2-pyridinecarboxylic chloride at a yield of 95.1%.

Example 2

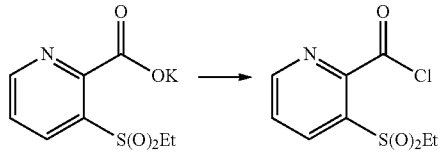

Under a nitrogen atmosphere, 25.00 g of xylene, 0.07 g of N,N-dimethylformamide, and 4.80 g of thionyl chloride were mixed and heated to 60° C., and then 5.00 g of potassium (3-ethylsulfonyl)-2-pyridinecarboxylate was added over 5 hours, followed by stirring at 60° C. for 4 hours. To the reaction solution, isobutylamine was added and quantitative determination was carried out by an internal reference method (internal reference substance; biphenyl) using high-performance liquid chromatography to obtain (3-ethylsulfonyl)-2-pyridinecarboxylic chloride at a yield of 96.9%.

Example 3

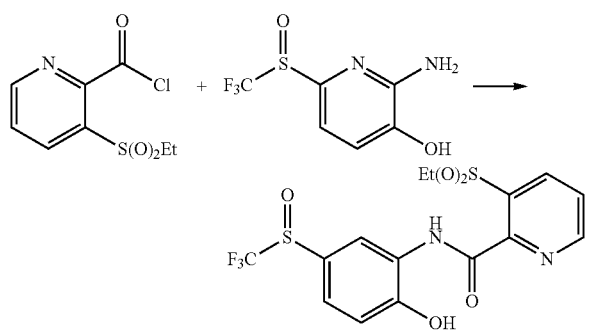

2-Amino-4-(trifluoromethylsulfinyl)phenol was prepared by the following method.

A mixture of 5.0 g of 2-nitro-4-(trifluoromethylsulfinyl) phenol, 0.50 g of palladium-carbon (Pd 5%), and 65 ml of ethanol was stirred under a hydrogen atmosphere at 35° C. for 6 hours. The reaction mixture allowed to cool down to room temperature was filtered through Celite (registered trademark) and water was added, followed by extraction with ethyl acetate. The organic layer was washed with water, dried over anhydrous sodium sulfate, and then concentrated under reduced pressure. The resulting solid was washed with chloroform to obtain 3.87 g of 2-amino-4-(trifuoromethyl-sulfinyl)phenol.

Under a nitrogen atmosphere, 1.80 g of 2-amino-4-(trif-luoromethylsulfinyl)phenol and 9.00 g of tetrahydrofuran were mixed and cooled to 0° C., and then a mixture of 1.95 g of (3-ethylsulfonyl)-2-pyridinecarboxylic chloride and 3.90 g of xylene was added dropwise over one hour, followed by stirring at 0° C. for 4 hours. To the reaction mixture, an aqueous saturated sodium hydrogen carbonate solution was added and the mixture was extracted with ethyl acetate, and then the organic layer was concentrated under reduced pressure to obtain 3-ethylsulfonyl-N-[2-hydroxy-5-(trifluoromethylsulfinyl)phenyl]picolinamide at a yield of 95.6%. $^1$H-NMR (DMSO-$d_6$) δ: 11.47 (1H, brs), 10.42 (1H, s), 8.97 (1H, dd), 8.74 (1H, s), 8.43 (1H, d), 7.88 (1H, dd), 7.58 (1H, dd), 7.25 (1H, d), 3.68 (2H, q), 1.18 (3H, t).

Example 4

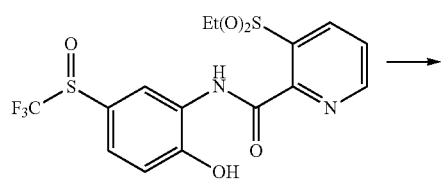

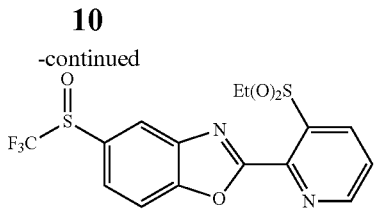

Under a nitrogen atmosphere, a mixture of 1.00 g of 3-ethylsulfonyl-N-[2-hydroxy-5-(trifluoromethylsulfinyl) phenyl]picolinamide, 0.66 g of p-toluenesulfonic acid monohydrate, and 5.00 g of xylene was dehydrated under reflux at 155° C. for 20 hours. The reaction mixture allowed to cool down to room temperature was added to an aqueous saturated sodium hydrogen carbonate solution. After separation, 5.00 g of heptane was added to the organic layer and cooling crystallization was carried out to obtain 2-(3-ethyl-sulfonyl pyridin-2-yl)-5-(trifluoromethylsulfinyl)benzox-azole at a yield of 88.2%.

$^1$H-NMR (CDCl$_3$) δ: 9.04 (1H, dd), 8.61 (1H, dd), 8.35 (1H, d), 7.96-7.86 (2H, m), 7.77 (1H, dd), 4.01 (2H, q), 1.44 (3H, t).

Example 5

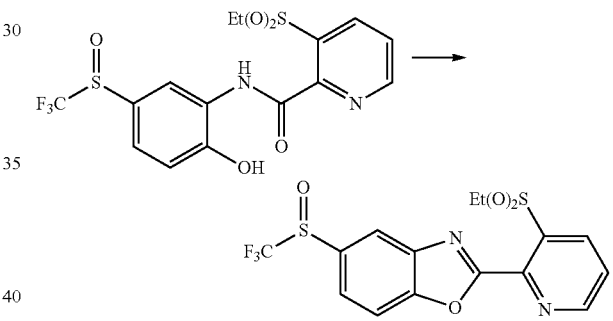

Under a nitrogen atmosphere, a mixture of 0.30 g of 3-ethylsulfonyl-N-[2-hydroxy-5-(trifluoromethylsulfinyl) phenyl]picolinamide, 0.20 g of p-toluenesulfonic acid monohydrate, and 1.50 g of mesitylene was dehydrated under reflux at 180° C. for 7 hours. The reaction mixture allowed to cool down to room temperature was added to an aqueous saturated sodium hydrogen carbonate solution. After separation, the resulting organic layer was analyzed by internal reference method (internal reference substance; biphenyl) using high-performance liquid chromatography to obtain 2-(3-ethylsulfonyl pyridin-2-yl)-5-(trifluoromethyl-sulfinyl)benzoxazole at a yield of 81.8%.

Example 6

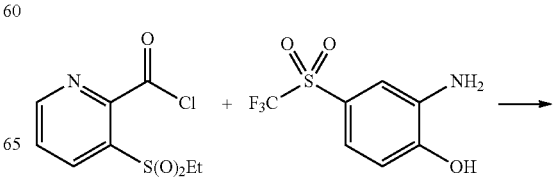

-continued

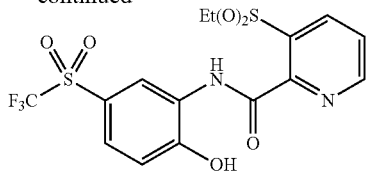

Under a nitrogen atmosphere, 1.80 g of 2-amino-4-(trifluoromethylsulfonyl)phenol and 9.00 g of tetrahydrofuran were mixed. After cooling to 0° C., a mixture of 1.91 g of (3-ethylsulfonyl)-2-pyridinecarboxylic chloride and 3.82 g of xylene was added dropwise over one hour, followed by stirring at 0° C. for 4 hours. To the reaction mixture, an aqueous saturated sodium hydrogen carbonate solution was added and the mixture was extracted with ethyl acetate, and then the organic layer was concentrated under reduced pressure to obtain 3-ethylsulfonyl-N-[2-hydroxy-5-(trifluoromethylsulfonyl)phenyl]picolinamide at a yield of 96.7%. $^1$H-NMR (DMSO-$d_6$) δ: 12.66 (1H, brs), 10.42 (1H, s), 8.97 (1H, dd), 8.85 (1H, d), 8.43 (1H, dd), 7.88 (1H, dd), 7.82 (1H, dd), 7.32 (1H, d), 3.68 (2H, q), 1.19 (3H, t).

Example 7

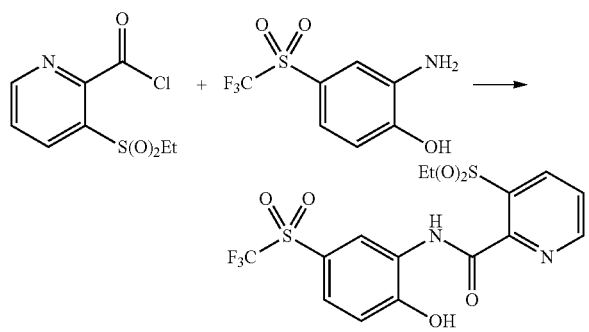

Under a nitrogen atmosphere, 10.00 g of 2-amino-4-(trifluoromethylsulfonyl)phenol and 50.00 g of tetrahydrofuran were mixed and cooled to 0° C., and then a mixture of 12.35 g of (3-ethylsulfonyl)-2-pyridinecarboxylic chloride and 27.00 g of tetrahydrofuran was added dropwise over one hour, followed by stirring at 0° C. for 4 hours. To the reaction mixture, an aqueous saturated sodium hydrogen carbonate solution was added, and then the mixture was concentrated under reduced pressure. The residue was extracted with ethyl acetate and the organic layer was concentrated under reduced pressure to obtain 3-ethylsulfonyl-N-[2-hydroxy-5-(trifluoromethylsulfonyl)phenyl]picolinamide at a yield of 93.4%.

Example 8

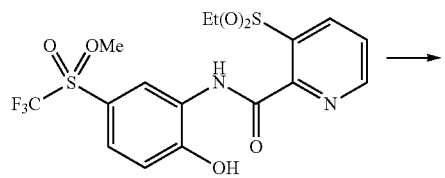

-continued

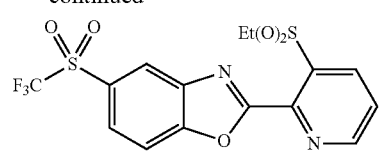

Under a nitrogen atmosphere, a mixture of 1.00 g of 3-ethylsulfonyl-N-[2-hydroxy-5-(trifluoromethylsulfonyl)phenyl]picolinamide, 0.62 g of p-toluenesulfonic acid monohydrate, and 5.00 g of xylene was dehydrated under reflux at 155° C. for 15 hours. The reaction mixture allowed to cool down to room temperature was added to an aqueous saturated sodium hydrogen carbonate solution. After separation, 5.00 g of heptane was added to the organic layer and cooling crystallization was carried out to obtain 2-(3-ethylsulfonylpyridin-2-yl)-5-(trifluoromethylsulfonyl) benzoxazole at a yield of 86.5%.

$^1$H-NMR (CDCl$_3$) δ: 9.05 (1H, dd), 8.61 (1H, dd), 8.59 (1H, d), 8.17 (1H, dd), 7.96 (1H, d), 7.80 (1H, dd), 3.98 (2H, q), 1.45 (3H, t).

Example 9

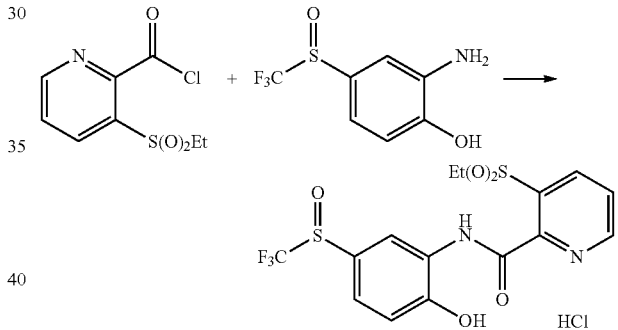

Under a nitrogen atmosphere, 2.70 g of 2-amino-4-(trifluoromethylsulfinyl)phenol and 8.10 g of tetrahydrofuran were mixed and cooled to 0° C., and then a mixture of 3.64 g of (3-ethylsulfonyl)-2-pyridinecarboxylic chloride and 3.64 g of tetrahydrofuran was added dropwise over 4 hours, followed by stirring at 0° C. for 12 hours. The reaction mixture was concentrated under reduced pressure to obtain 6.21 g of 3-ethylsulfonyl-N-[2-hydroxy-5-(trifluoromethylsulfinyl)phenyl]picolinamide hydrochloride at a yield of 96.7%.

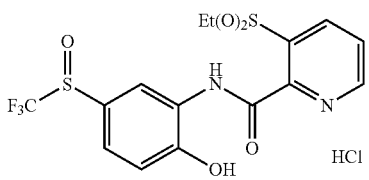

$^1$H-NMR (DMSO-$d_6$) δ: 12.56 (1H, brs), 10.40 (1H, s), 8.97 (1H, dd), 8.86 (1H, d), 8.44 (1H, dd), 7.88 (1H, dd), 7.81 (1H, dd), 7.42 (1H, d), 3.68 (2H, q), 1.20 (3H, t).

Example 10

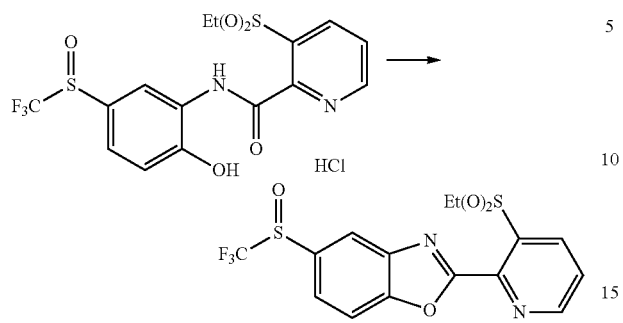

Under a nitrogen atmosphere, a mixture of 3.00 g of 3-ethylsulfonyl-N-[2-hydroxy-5-(trifluoromethylsulfinyl)phenyl]picolinamide hydrochloride, 1.24 g of p-toluenesulfonic acid monohydrate, and 15.00 g of xylene was dehydrated under reflux at 155° C. for 20 hours. The reaction mixture allowed to cool down to room temperature was added to an aqueous saturated sodium hydrogen carbonate solution. After separation, quantitative determination of the resulting organic layer was carried out by internal reference method (internal reference substance; biphenyl) using high-performance liquid chromatography to obtain 2-(3-ethylsulfonyl pyridin-2-yl)-5-(trifluoromethylsulfinyl)benzoxazole at a yield of 85.0%.

Example 11

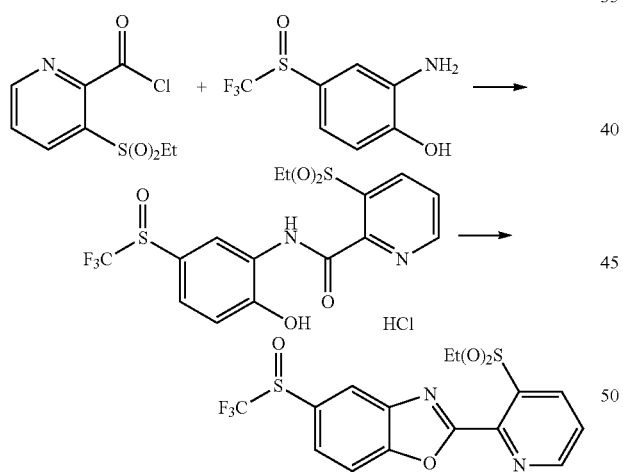

Under a nitrogen atmosphere, 3.00 g of 2-amino-4-(trifluoromethylsulfinyl)phenol and 12.00 g of tetrahydrofuran were mixed and cooled to 0° C., and then a mixture of 4.11 g of (3-ethylsulfonyl)-2-pyridinecarboxylic chloride and 7.00 g of xylene was added dropwise over 4 hours, followed by stirring at 0° C. for 12 hours. The reaction mixture was concentrated under reduced pressure and a mixture of 5.06 g of p-toluenesulfonic acid monohydrate and xylene 16.90 g of xylene was added to the resulting the residue, followed by dehydration under reflux at 155° C. for 24 hours. The reaction mixture allowed to cool down to room temperature was added to an aqueous saturated sodium hydrogen carbonate solution. After separation, quantitative determination of the resulting organic layer was carried out by internal reference method (internal reference substance; biphenyl) using high-performance liquid chromatography to obtain 2-(3-ethylsulfonylpyridin-2-yl)-5-(trifluoromethylsulfinyl)benzoxazole at a yield of 79.4%.

Example 12

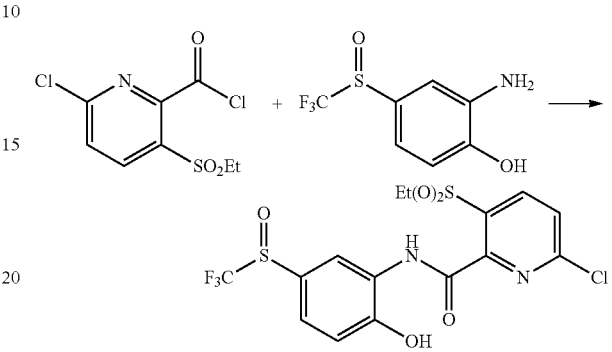

Under a nitrogen atmosphere, 4.33 g of 2-amino-4-(trifluoromethylsulfinyl)phenol and 34.72 g of tetrahydrofuran were mixed and cooled to 0° C., and then a mixture of 5.30 g of (3-ethylsulfonyl)-6-chloro-2-pyridinecarboxylic chloride and 10.60 g of tetrahydrofuran was added dropwise over one hour, followed by stirring at 0° C. for 4 hours. To the reaction mixture, an aqueous saturated sodium hydrogen carbonate solution was added and the mixture was extracted with ethyl acetate, and then the organic layer was concentrated under reduced pressure to obtain 3-ethylsulfonyl-N-[2-hydroxy-5-(trifluoromethylsulfinyl)phenyl]picolinamide at a yield of 99.2%.

$^1$H-NMR (DMSO-$d_6$) δ: 11.55 (1H, brs), 10.45 (1H, s), 8.65 (1H, s), 8.38 (1H, d), 7.96 (1H, d), 7.57 (1H, d), 7.26 (1H, d), 3.84 (2H, q), 1.32 (3H, t).

Example 13

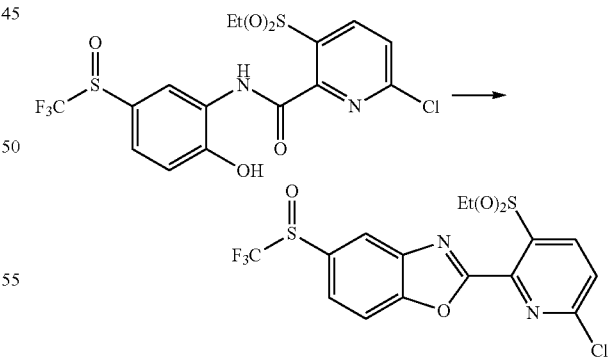

Under a nitrogen atmosphere, a mixture of 1.00 g of 3-ethylsulfonyl-6-chloro-N-[2-hydroxy-5-(trifluoromethylsulfinyl) phenyl]picolinamide, 0.74 g of p-toluenesulfonic acid monohydrate, and 5.21 g of chlorobenzene was dehydrated under reflux at 140° C. for 8 hours. The reaction mixture allowed to cool down to room temperature was added to an aqueous saturated sodium hydrogen carbonate solution. After separation, the organic layer was concentrated to obtain 0.95 g of 2-(6-chloro-3-ethylsulfonylpyridine-2-yl)-5-(trifluoromethylsulfinyl) benzoxazole.

$^1$H-NMR (CDCl$_3$) δ: 8.53 (1H, d), 8.36 (1H, d), 7.94 (1H, dd), 7.89 (1H, dd), 7.76 (1H, d), 4.01 (2H, q), 1.44 (3H, t).

Example 14

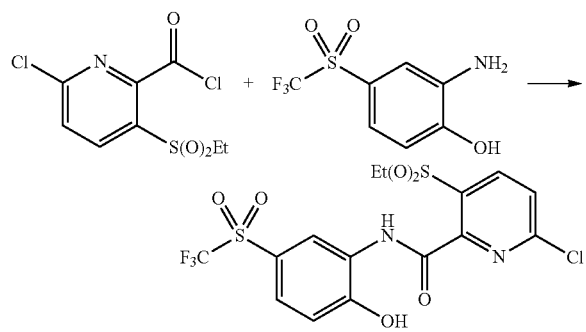

Under a nitrogen atmosphere, 4.58 g of 2-amino-4-(trifluoromethylsulfonyl)phenol and 36.82 g of tetrahydrofuran were mixed and cooled to 0° C., and then a mixture of 5.30 g of (3-ethylsulfonyl)-6-chloro-2-pyridinecarboxylic chloride and 10.60 g of tetrahydrofuran was added dropwise over one hour, followed by stirring at 0° C. for 4 hours. To the reaction mixture, an aqueous saturated sodium hydrogen carbonate solution was added and the mixture was extracted with ethyl acetate, and then the organic layer was concentrated under reduced pressure to obtain 3-ethylsulfonyl-6-chloro-N-[2-hydroxy-5-(trifluoromethylsulfonyl)phenyl]picolinamide at a yield of 98.4%.

$^1$H-NMR (DMSO-d$_6$) δ: 10.77 (1H, brs), 9.97 (1H, s), 9.09 (1H, s), 8.49 (1H, d), 7.85 (1H, d), 7.77 (1H, d), 7.18 (1H, d), 3.80 (2H, q), 1.22 (3H, t).

Example 15

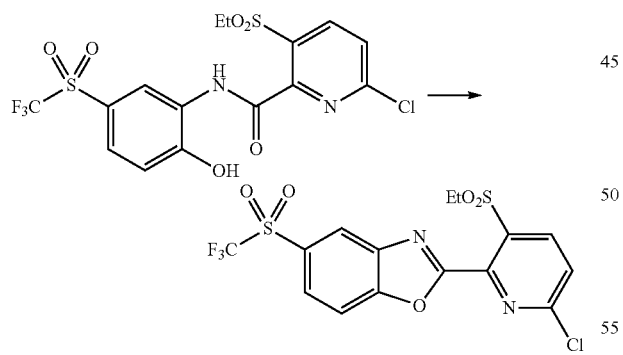

Under a nitrogen atmosphere, a mixture of 1.01 g of 3-ethylsufonyl-6-chloro-N-[2-hydroxy-5-(trifluoromethylsulfonyl) phenyl]picolinamide, 0.72 g of p-toluenesulfonic acid monohydrate, and 5.32 g of chlorobenzene was dehydrated under reflux at 140° C. for 8 hours. The reaction mixture allowed to cool down to room temperature was added to an aqueous saturated sodium hydrogen carbonate solution. After separation, the organic layer was concentrated to obtain 0.95 g of 2-(6-chloro-3-ethylsulfonylpyridine-2-yl)-5-(trifluoromethylsulfonyl) benzoxazole.

$^1$H-NMR (CDCl$_3$) δ: 8.59 (1H, d), 8.54 (1H, d), 8.18 (1H, dd), 7.98 (1H, d), 7.79 (1H, d), 3.98 (2H, q), 1.45 (3H, t).

Comparative Example 1

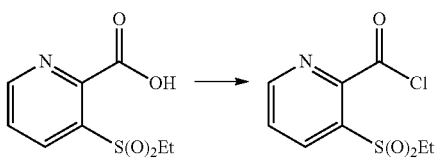

Under a nitrogen atmosphere, 3.00 g of (3-ethylsulfonyl)-2-pyridinecarboxylic acid, 9.00 g of toluene, and 0.11 g of N,N-dimethylformamide were mixed and heated to 60° C., and then 2.03 g of thionyl chloride was added dropwise over 5 hours, followed by stirring at 60° C. for 4 hours. To the reaction solution, n-butanol was added and analysis was carried out using high-performance liquid chromatography to obtain (3-ethylsulfonyl)-2-pyridinecarboxylic chloride at a yield of 65.3%.

INDUSTRIAL APPLICABILITY

The present invention provides a method for producing a compound represented by formula (4) which has an excellent control efficacy against pests.

The invention claimed is:

1. A method for producing a compound represented by formula (4), which comprises a step A of reacting a compound represented by formula (2):

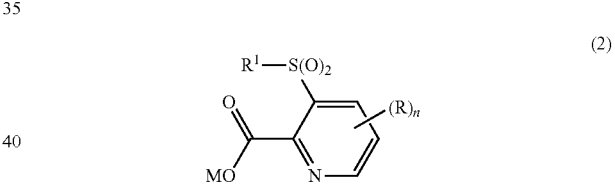

(2)

wherein R$^1$ represents a chain hydrocarbon group having 1 to 6 carbon atoms which is optionally halogenated, or an alicyclic hydrocarbon group having 3 to 6 carbon atoms which is optionally halogenated, each R independently represents a chain hydrocarbon group having 1 to 6 carbon atoms which is optionally halogenated, or a halogen atom, n represents 0, 1, 2, or 3, and M represents sodium, potassium, or lithium, with thionyl chloride to obtain a compound represented by formula (1):

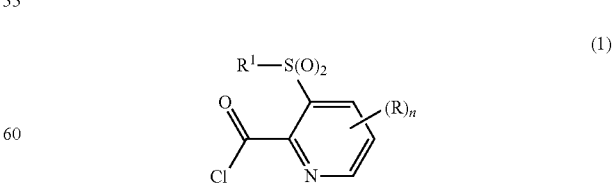

(1)

wherein R$^1$, R, and n have the same meanings as defined above;

a step B of reacting the compound represented by formula (1) with a compound represented by formula (5):

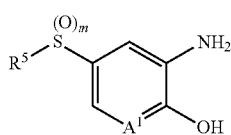

(5)

wherein A¹ represents a nitrogen atom or =CH—,
R⁵ represents a chain hydrocarbon group having 1 to 6 carbon atoms which is optionally halogenated, or an alicyclic hydrocarbon group having 3 to 6 carbon atoms which is optionally halogenated, and m represents 1 or 2,
to produce a compound represented by formula (3):

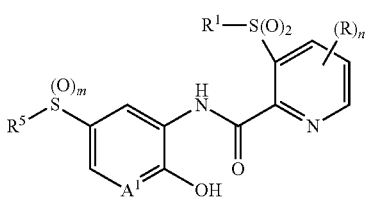

(3)

wherein R¹, R, R⁵, A¹, m, and n have the same meanings as defined above; and
a step C of reacting the compound represented by formula (3) or an acid salt thereof in the presence of an acid at 100° C. to 180° C. to obtain the compound represented by formula (4):

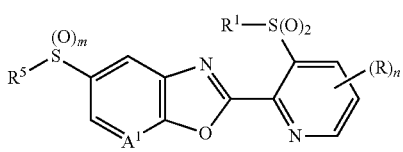

(4)

wherein R¹, R, R⁵, A¹, m, and n have the same meanings as defined above.

2. The method according to claim 1, wherein the acid in the step C is a sulfonic acid compound.
3. The method according to claim 1, wherein the acid in the step C is p-toluenesulfonic acid.
4. The method according to claim 1, wherein the acid in the step C is methanesulfonic acid.
5. A method for producing a compound represented by formula (3) or an acid salt thereof, which comprises a step A of reacting a compound represented by formula (2):

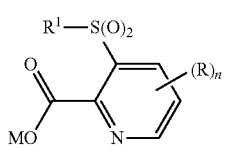

(2)

wherein R¹ represents a chain hydrocarbon group having 1 to 6 carbon atoms which is optionally halogenated, or an alicyclic hydrocarbon group having 3 to 6 carbon atoms which is optionally halogenated, each R independently represents a chain hydrocarbon group having 1 to 6 carbon atoms which is optionally halogenated, or a halogen atom, n represents 0, 1, 2, or 3, and
M represents sodium, potassium, or lithium,
with thionyl chloride to obtain a compound represented by formula (1):

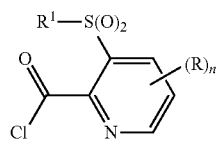

(1)

wherein R¹, R, and n have the same meanings as defined above; and
a step B of reacting the compound represented by formula (1) with a compound represented by formula (5):

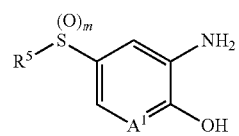

(5)

wherein A¹ represents a nitrogen atom or =CH—,
R⁵ represents a chain hydrocarbon group having 1 to 6 carbon atoms which is optionally halogenated, or an alicyclic hydrocarbon group having 3 to 6 carbon atoms which is optionally halogenated, and
m represents 1 or 2,
to produce the compound represented by formula (3):

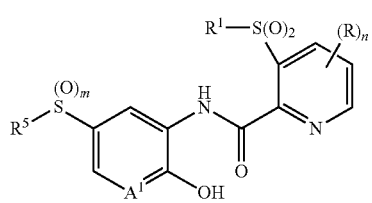

(3)

wherein R¹, R, R⁵, A¹, m, and n have the same meanings as defined above.

6. The method according to claim 1, wherein the solvent used in the step B contains comprises an ether solvent.
7. A method for producing a compound represented by formula (1), which comprises a step A of reacting a compound represented by formula (2):

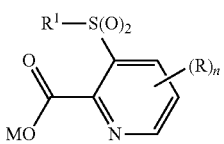

(2)

wherein R¹ represents a chain hydrocarbon group having 1 to 6 carbon atoms which is optionally halogenated, or an alicyclic hydrocarbon group having 3 to 6 carbon atoms which is optionally halogenated, each R independently represents a chain hydrocarbon group having 1 to 6 carbon atoms which is optionally halogenated, or a halogen atom, n represents 0, 1, 2, or 3, and M represents sodium, potassium, or lithium, with thionyl chloride to obtain the compound represented by formula (1):

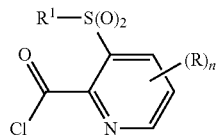

(1)

wherein $R^1$, R, and n have the same meanings as defined above.

* * * * *